United States Patent
Furuhashi et al.

(10) Patent No.: US 12,083,257 B2
(45) Date of Patent: Sep. 10, 2024

(54) BLOOD PURIFICATION APPARATUS

(71) Applicant: Nikkiso Company Limited, Tokyo (JP)

(72) Inventors: Tomohiro Furuhashi, Shizuoka (JP); Yuki Eda, Shizuoka (JP); Masaaki Ohta, Shizuoka (JP); Kazuhide Ono, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 733 days.

(21) Appl. No.: 17/213,378

(22) Filed: Mar. 26, 2021

(65) Prior Publication Data

US 2021/0213189 A1    Jul. 15, 2021

Related U.S. Application Data

(63) Continuation of application No. PCT/JP2019/043765, filed on Nov. 7, 2019.

(30) Foreign Application Priority Data

Nov. 8, 2018 (JP) ................. 2018-210892

(51) Int. Cl.
*A61M 1/34* (2006.01)
*A61M 1/36* (2006.01)
*A61M 39/24* (2006.01)

(52) U.S. Cl.
CPC .......... *A61M 1/342* (2013.01); *A61M 1/3601* (2014.02); *A61M 1/3638* (2014.02); *A61M 39/24* (2013.01); *A61M 2205/3331* (2013.01)

(58) Field of Classification Search
CPC .. A61M 1/342; A61M 1/3434; A61M 1/3638; A61M 39/24
See application file for complete search history.

(56) References Cited

U.S. PATENT DOCUMENTS 8,894,600 B2   11/2014 Kelly et al.
2005/0131331 A1   6/2005 Kelly et al.
(Continued)

FOREIGN PATENT DOCUMENTS

JP   S55-112891 A   9/1980
JP   S56-027257 A   3/1981
(Continued)

OTHER PUBLICATIONS

European Search Report for Application No. 19 882 183.7, dated Apr. 25, 2022, 8 pgs.

*Primary Examiner* — Bradley R Spies
(74) *Attorney, Agent, or Firm* — Young Basile Hanlon & MacFarlane, P.C.

(57) ABSTRACT

A blood purification apparatus capable of performing pre-substitution and post-substitution simultaneously is provided. A patient's blood flows through an arterial blood circuit and reaches a dialyzer. The blood purified by the dialyzer flows through a venous blood circuit and returns into the patient. A first substitution pump delivers substitution fluid through a substitution line to a branching point. A pre-substitution line connects the branching point and the arterial blood circuit to each other and is provided with a second substitution pump at a halfway position thereof. A post-substitution line connects the branching point and the venous blood circuit to each other and is provided with a check valve at a halfway position thereof. When the two pumps are activated simultaneously, the substitution fluid is supplied to the arterial blood circuit (pre-substitution). When only the first substitution pump is activated, the substitution fluid is supplied to the venous blood circuit (post-substitution). When the flow rate of the second substitution pump is set higher than the flow rate of the first (Continued)

substitution pump, pre-substitution and post-substitution are performed simultaneously.

5 Claims, 4 Drawing Sheets

(56) References Cited

U.S. PATENT DOCUMENTS

| | | | |
|---|---|---|---|
| 2015/0359955 A1 | 12/2015 | Wolff et al. | |
| 2017/0296727 A1* | 10/2017 | Burbank | A61M 1/3607 |
| 2018/0140766 A1* | 5/2018 | Mochizuki | A61M 1/1607 |

FOREIGN PATENT DOCUMENTS

| | | |
|---|---|---|
| JP | 2002-126075 A | 5/2002 |
| JP | 2017-023441 A | 2/2017 |
| WO | 2015/192927 A1 | 12/2015 |

\* cited by examiner

[Fig. 1]
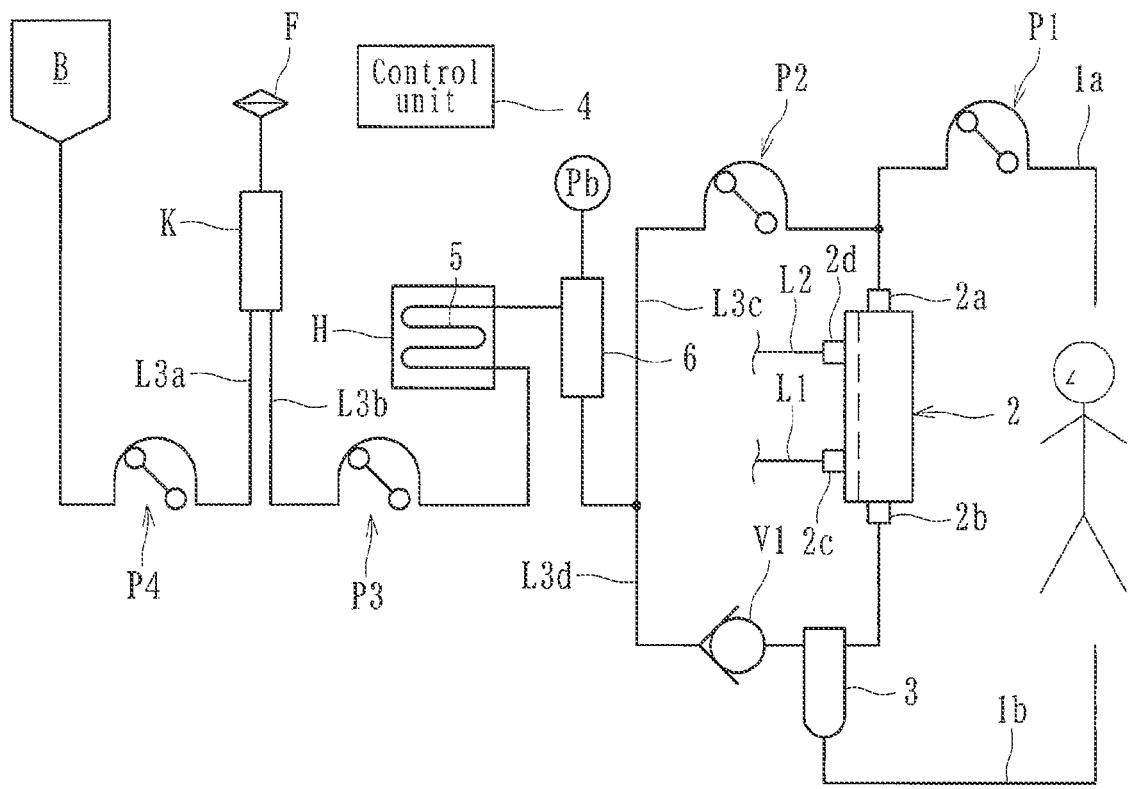
[Fig. 2]
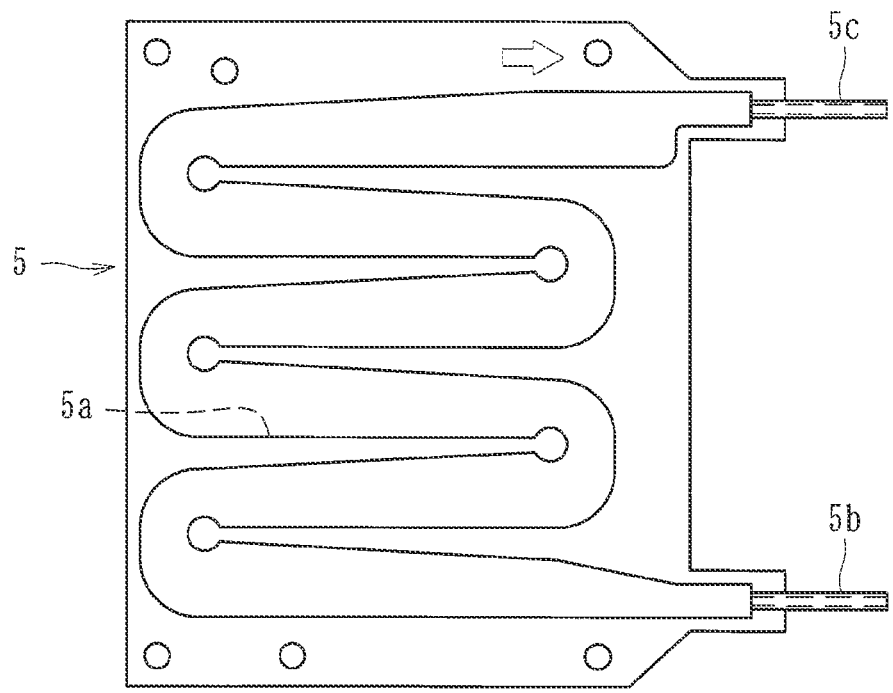

[Fig. 3]
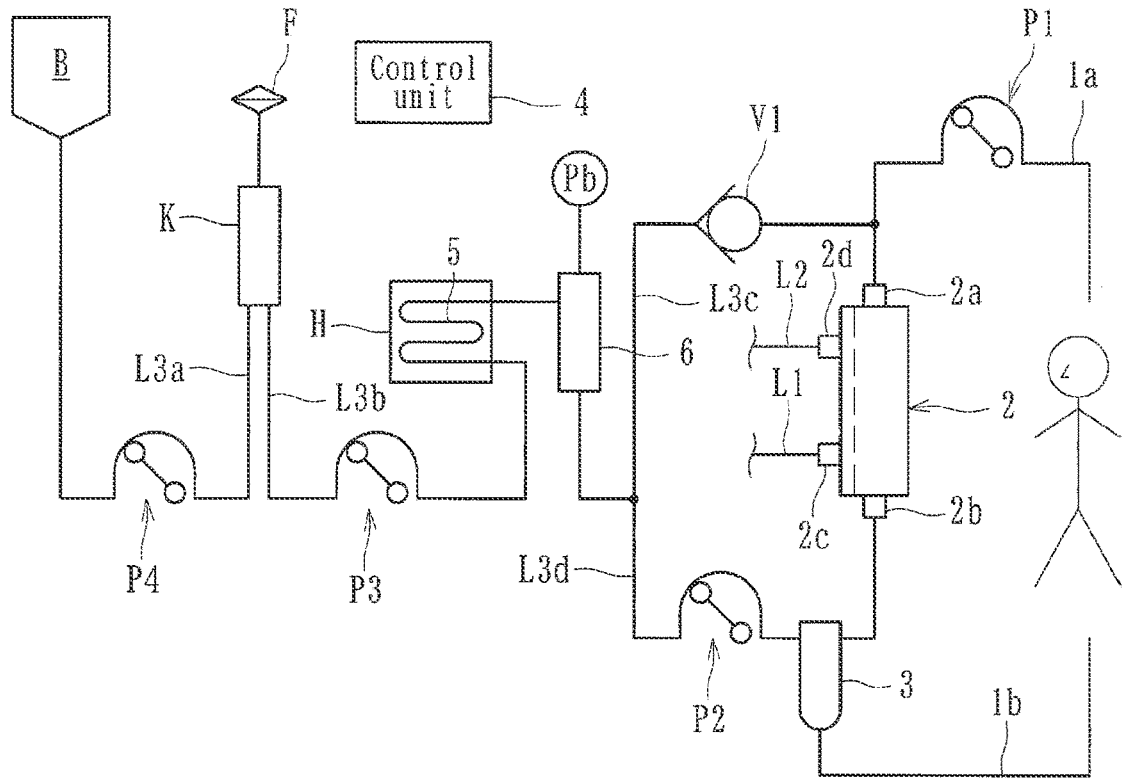
[Fig. 4]
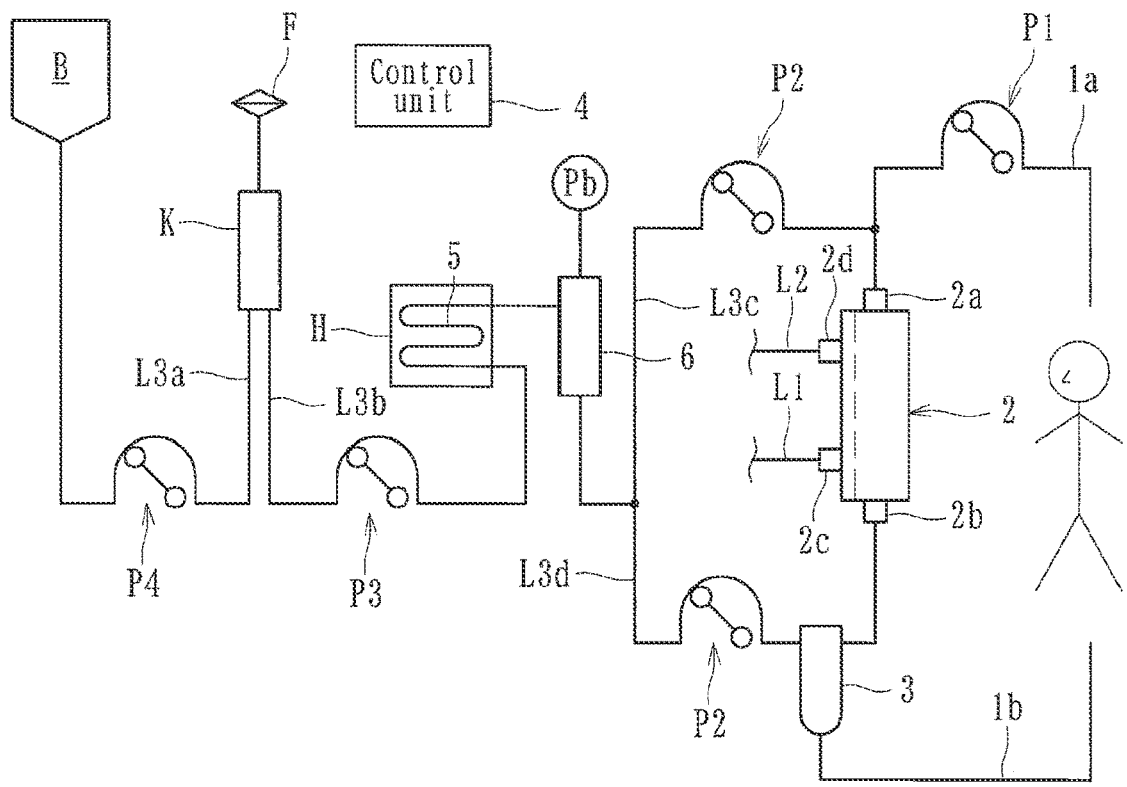

[Fig. 5]
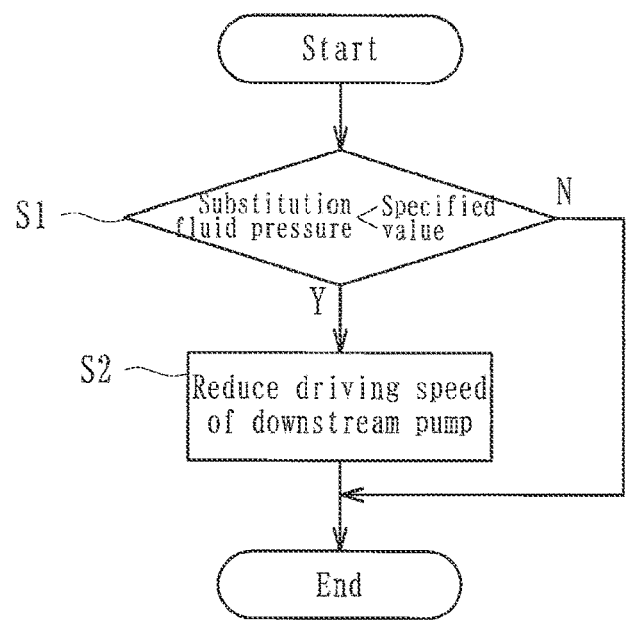
[Fig. 6]
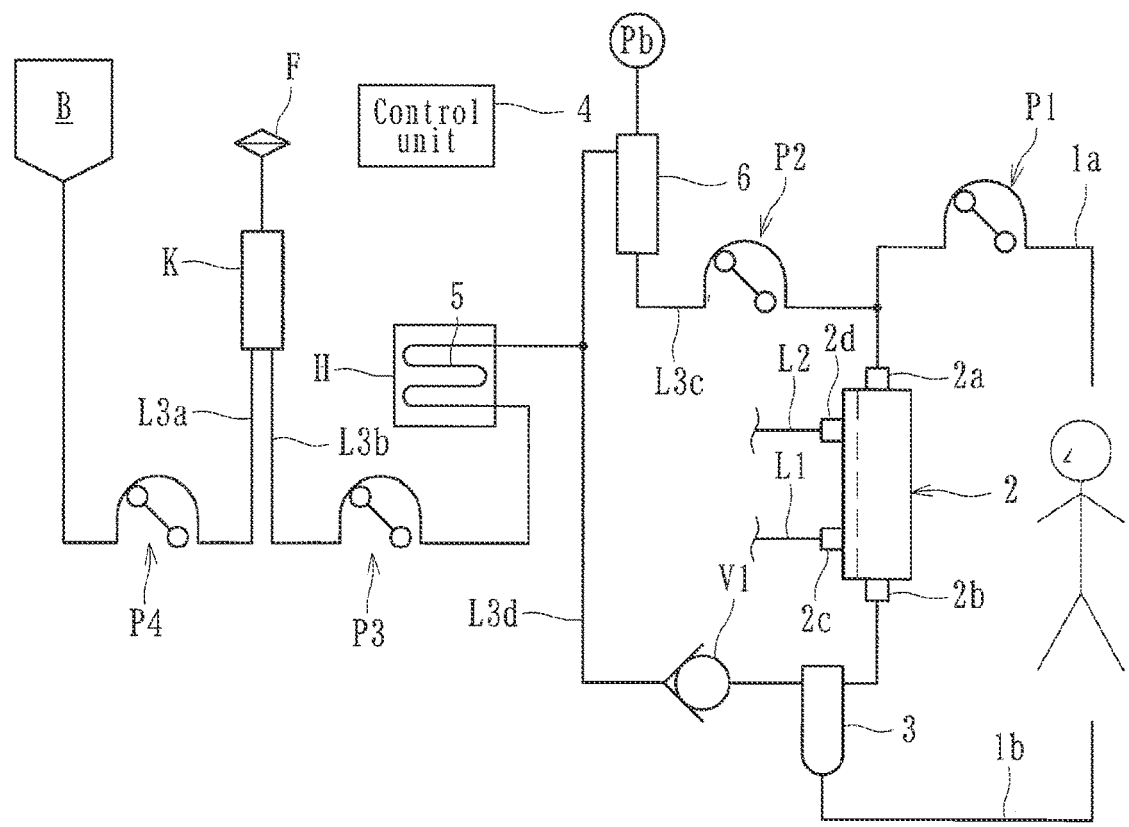

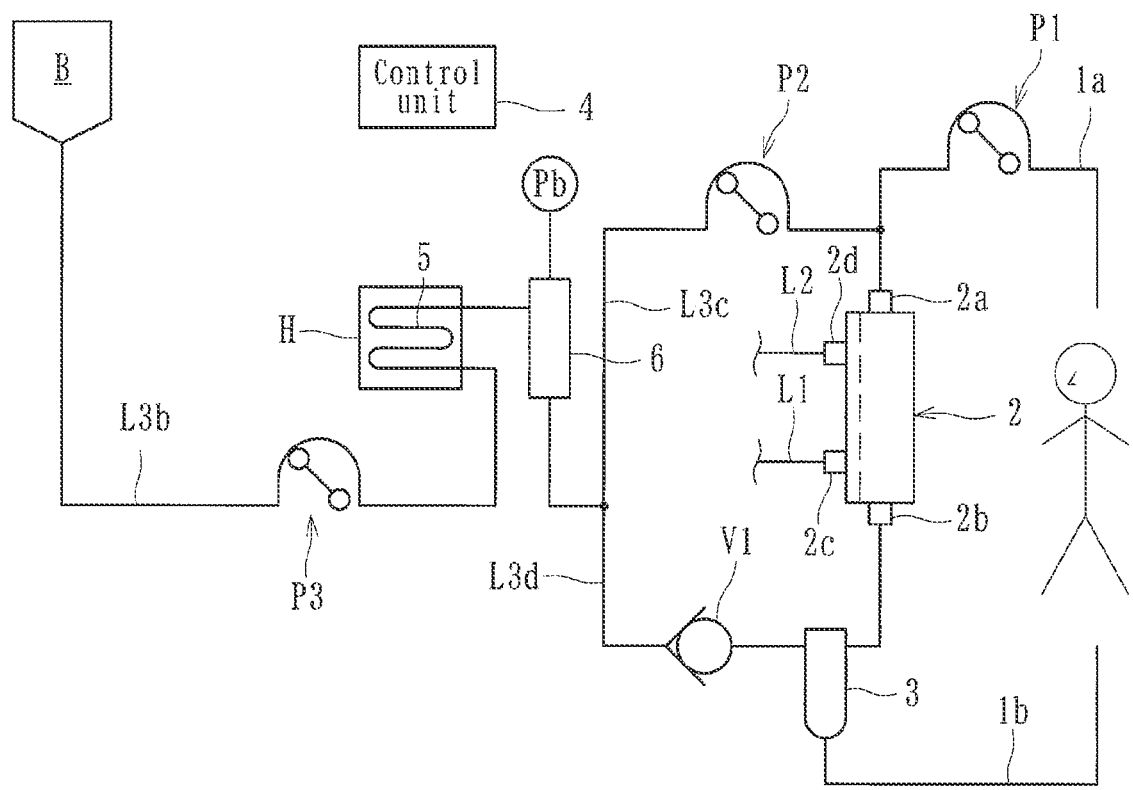
[Fig. 7]

BLOOD PURIFICATION APPARATUS

CROSS-REFERENCE TO RELATED APPLICATION(S)

This application is a continuation of International Application No. PCT/JP2019/043765, filed on Nov. 7, 2019, which claims priority to Japanese Application No. 2018-210892, filed on Nov. 8, 2018, the entire disclosures of which are hereby incorporated by reference.

FIELD

The present teachings relate to a blood purification apparatus for purifying blood of a patient while causing the blood to extracorporeally circulate.

BACKGROUND

In general, a blood purification apparatus for giving dialysis treatment includes an arterial blood circuit and a venous blood circuit that form a blood circuit for causing blood of a patient to extracorporeally circulate, a blood purifier for purifying the blood extracorporeally circulating through the blood circuit, and an apparatus body provided with various treatment devices, such as a blood pump, for performing blood purification treatment with the blood circuit and the blood purifier. The arterial blood circuit and the venous blood circuit are each provided with a vascular access catheter or a puncture needle (an arterial puncture needle or a venous puncture needle) that is attachable to a distal end thereof.

For example, after the patient is punctured with the arterial puncture needle and the venous puncture needle, the blood pump is activated. Thus, blood of the patient flows through the arterial blood circuit and the venous blood circuit. In this flowing process, the blood is purified by the blood purifier. In dialysis treatment, a dialysate introduction line for introducing dialysate into the blood purifier and a waste-liquid drain line for draining waste liquid from the blood purifier are connected to the blood purifier.

Methods established for blood purification treatment include hemodialysis (HD) in which dialysate is made to flow through dialysate flow routes provided in the blood purifier and substances in the blood are removed by the effect of diffusion through blood purification membranes, hemofiltration (HF) in which water and substances in the blood are removed by the effect of ultrafiltration pressure generated in the blood purifier and an amount of substitution fluid that is equal to the amount of water removed is infused into the blood, and hemodiafiltration (HDF) in which hemodialysis (HD) and hemofiltration (HF) are performed simultaneously. In particular, when blood purification treatment is given to a patient having a disease such as acute renal failure, the treatment method needs to be switched among hemodialysis (HD), hemofiltration (HF), and hemodiafiltration (HDF) during a series of treatment steps in accordance with the patient's condition.

In hemofiltration (HF) and hemodiafiltration (HDF), any of the following are selectively performed: pre-substitution in which substitution fluid is introduced into a portion (the arterial blood circuit) on the upstream side with respect to the blood purifier, post-substitution in which substitution fluid is introduced into a portion (the venous blood circuit) on the downstream side with respect to the blood purifier, and pre- and post-substitution in which substitution fluid is introduced into both portions (the arterial blood circuit and the venous blood circuit) on the upstream side and the downstream side with respect to the blood purifier. Hence, there is a recent demand for a blood purification apparatus in which the treatment method is switchable among hemodialysis (HD), hemofiltration (HF), and hemodiafiltration (HDF) and the substitution method is arbitrarily selectable from pre-substitution, post-substitution, and pre- and post-substitution.

To meet the above demand, an apparatus according to a known proposal includes a pre-substitution line through which substitution fluid is introduced into an arterial blood circuit for pre-substitution, a post-substitution line through which substitution fluid is introduced into a venous blood circuit for post-substitution, and a substitution line having one end connected to a substitution-fluid source capable of supplying the substitution fluid and the other end connected to the pre-substitution line and to the post-substitution line, the substitution line allowing the substitution fluid in the substitution-fluid source to be introduced into the arterial blood circuit or the venous blood circuit through the pre-substitution line or the post-substitution line, the pre-substitution line and the post-substitution line each being provided with a substitution pump (see PTL 1, for example).

Specifically, in the known blood purification apparatus, the pre-substitution line is provided with a peristaltic pump as a substitution pump, and the post-substitution line is provided with a peristaltic pump as a substitution pump. To perform pre-substitution, the substitution pump provided to the pre-substitution line is activated to introduce the substitution fluid in the substitution-fluid source into the arterial blood circuit. To perform post-substitution, the substitution pump provided to the post-substitution line is activated to introduce the substitution fluid in the substitution-fluid source into the venous blood circuit. To perform pre-substitution and post-substitution simultaneously, both the substitution pump for the pre-substitution line and the substitution pump for the post-substitution line are activated to introduce the substitution fluid in the substitution-fluid source into both the arterial blood circuit and the venous blood circuit.

PTL 1: Japanese Unexamined Patent Application Publication No. 2002-126075 is incorporated by reference herein for all purposes.

SUMMARY

The above known blood purification apparatus includes the substitution pumps provided to the pre-substitution line and the post-substitution line, respectively. Therefore, when pre-substitution and post-substitution are performed simultaneously, both the substitution pump for the pre-substitution line and the substitution pump for the post-substitution line are activated. Consequently, the flow rate error occurring in the substitution pump for the pre-substitution line and the flow rate error occurring in the substitution pump for the post-substitution line are added up to a greater flow rate error. Therefore, it is difficult to correctly grasp the amount of substitution fluid consumed from the substitution-fluid source.

Another problem arises in an apparatus including a pre-substitution line and a post-substitution line each being provided with a substitution pump, and a heating bag in which a flow route connected to the substitution line is provided to be heated. If the heating bag is provided on the upstream side with respect to the two substitution pumps in the direction of substitution-fluid delivery, the heating bag is affected by negative pressure. Therefore, the heating bag needs to be made of a hard material, which costs high. On the other hand, if the heating bag is provided on the downstream side with respect to the two substitution pumps in the direction of fluid delivery, the heating bag is not affected by negative pressure. Instead, two heating bags are necessary, which increases the heating-bag cost.

The present teachings have been conceived in view of the above circumstances and aims to provide a blood purification apparatus with which pre-substitution and post-substitution can be performed in a good manner and the amount of substitution fluid consumed from a substitution-fluid source can be grasped correctly even in a case where pre-substitution and post-substitution are performed simultaneously. The present invention additionally aims to achieve a reduction in the heating-bag cost.

Variation 1 comprises a blood purification apparatus including: a blood circuit including an arterial blood circuit and a venous blood circuit and that allows a patient's blood to extracorporeally circulate, with a blood purifier that is interposed between the arterial blood circuit and the venous blood circuit and purifies the patient's blood; a pre-substitution line through which substitution fluid is introduced into the arterial blood circuit for pre-substitution; a post-substitution line through which the substitution fluid is introduced into the venous blood circuit for post-substitution; a substitution line having one end connected to a substitution-fluid source capable of supplying the substitution fluid, and an other end connected to the pre-substitution line and to the post-substitution line; substitution pumps that deliver the substitution fluid in the substitution-fluid source from the substitution line through at least one of the pre-substitution line and the post-substitution line to at least one of the arterial blood circuit and the venous blood circuit; and a control unit that controls the substitution pumps. The substitution pumps include a first substitution pump provided to the substitution line, and a second substitution pump provided to the at least one of the pre-substitution line and the post-substitution line.

Variation 2 may comprise the blood purification apparatus according to variation 1, the second substitution pump is provided to only one of the pre-substitution line and the post-substitution line.

Variation 3 may comprise the blood purification apparatus according to variation 1 or 2 further includes a heating bag to be heated by a heating device and including a portion of the substitution line, the heating bag being attached to a position of the substitution line that is between the first substitution pump and a branching part of the pre-substitution line and the post-substitution line.

Variation 4 may comprise the blood purification apparatus according to variation 3, the substitution line is provided with an air-trap chamber at a position between the heating device and the arterial blood circuit or the venous blood circuit, the air-trap chamber being capable of trapping bubbles in the substitution fluid.

Variation 5 may comprise the blood purification apparatus according to any of variations 1 to 4, the first substitution pump and the second substitution pump are each a peristaltic pump that delivers liquid by squeezing a flexible tube forming a flow route for the substitution fluid.

Variation 6 may comprise the blood purification apparatus according to any of variations 1 to 5, one of the pre-substitution line and the post-substitution line is provided with the second substitution pump, and an other is provided with a check valve.

Variation 7 may comprise the blood purification apparatus according to variation 6 further includes a pressure sensor that detects a fluid pressure in a portion between the first substitution pump and the second substitution pump in the substitution line, the pre-substitution line, and the post-substitution line. The control unit corrects a driving speed of the first substitution pump or the second substitution pump in accordance with the fluid pressure detected by the pressure sensor.

According to variation 1, the substitution pumps include the first substitution pump provided to the substitution line, and the second substitution pump provided to the at least one of the pre-substitution line and the post-substitution line. Therefore, pre-substitution and post-substitution can be performed in a good manner. Furthermore, even in a case where pre-substitution and post-substitution are performed simultaneously, the amount of substitution fluid consumed from the substitution-fluid source can be grasped correctly.

According to variation 2, the second substitution pump is provided to only one of the pre-substitution line and the post-substitution line. Therefore, unlike a case where the second substitution pump is provided to each of the pre-substitution line and the post-substitution line, there is no need to synchronize two second substitution pumps. Consequently, the error in the amount of substitution fluid consumed through the pre-substitution line and the amount of substitution fluid consumed through the post-substitution line can be reduced.

According to variation 3, the blood purification apparatus further includes the heating bag to be heated by the heating device and including the portion of the substitution line, the heating bag being attached to the position of the substitution line that is between the first substitution pump and the branching part of the pre-substitution line and the post-substitution line. Therefore, the heating bag can be provided regardless of whether the material thereof is soft or hard. Furthermore, the number of heating bags can be reduced, leading to a reduction in the heating-bag cost.

According to variation 4, the substitution line is provided with the air-trap chamber at the position between the heating device and the arterial blood circuit or the venous blood circuit, the air-trap chamber being capable of trapping bubbles in the substitution fluid. Therefore, bubbles generated in the substitution fluid when the substitution fluid is heated by the heating device can be assuredly trapped and removed by the air-trap chamber.

According to variation 5, the first substitution pump and the second substitution pump are each a peristaltic pump that delivers liquid by squeezing a flexible tube forming a flow route for the substitution fluid. Therefore, the flow route for the substitution fluid can be closed by stopping the peristaltic pumps, without providing any separate clamping units or the like.

According to variation 6, one of the pre-substitution line and the post-substitution line is provided with the second substitution pump, and the other is provided with the check valve. Therefore, even if a negative pressure is generated between the first substitution pump and the second substitution pump, the check valve can prevent the blood in the blood circuit from being taken into the pre-substitution line or the post-substitution line.

According to variation 7, the blood purification apparatus further includes the pressure sensor that detects the fluid pressure in the portion between the first substitution pump and the second substitution pump in the substitution line, the pre-substitution line, and the post-substitution line. Furthermore, the control unit corrects the driving speed of the first substitution pump or the second substitution pump in accordance with the fluid pressure detected by the pressure sensor.

Therefore, even if a negative pressure or a positive pressure is generated in the portion of the flow route for the substitution fluid between the first substitution pump and the second substitution pump in the substitution line, the pre-substitution line, and the post-substitution line, the negative pressure or the positive pressure can be removed by correcting the driving speed of the first substitution pump or the second substitution pump.

BRIEF DESCRIPTION OF THE DRAWINGS

FIG. 1 is a schematic diagram of a blood purification apparatus according to an embodiment of the present invention.

FIG. 2 is a front view of a heating bag included in the blood purification apparatus.

FIG. 3 is a schematic diagram of a blood purification apparatus according to another embodiment of the present invention (in which a pre-substitution line is provided with a check valve, and a post-substitution line is provided with a second substitution pump).

FIG. 4 is a schematic diagram of a blood purification apparatus according to yet another embodiment of the present invention (in which a pre-substitution line and a post-substitution line are each provided with a second substitution pump).

FIG. 5 is a flow chart of a control process executed by a control unit of the blood purification apparatus.

FIG. 6 is a schematic diagram of a blood purification apparatus according to yet another embodiment of the present invention.

FIG. 7 is a schematic diagram of a blood purification apparatus according to yet another embodiment of the present invention.

DETAILED DESCRIPTION

Embodiments of the present invention will now be described specifically with reference to the drawings.

A blood purification apparatus according to an embodiment is applied to a hemodialysis apparatus for purifying blood of a patient while causing the blood to extracorporeally circulate. As illustrated in FIG. 1, the apparatus includes a blood circuit 1 including an arterial blood circuit 1a and a venous blood circuit 1b, a dialyzer 2 (a blood purifier) provided between the arterial blood circuit 1a and the venous blood circuit 1b and that purifies blood flowing through the blood circuit 1, a dialysate introduction line L1, a waste-liquid drain line L2, a first substitution line L3a, a second substitution line L3b, a pre-substitution line L3c, a post-substitution line L3d, a blood pump P1, a substitution-fluid transfer pump P4, a first substitution pump P3, a second substitution pump P2, a substitution-fluid temporary chamber K, a control unit 4, and a heating device H. Note that reference sign Pb given in the drawing denotes a pressure sensor. The blood pump P1, the substitution-fluid transfer pump P4, the first substitution pump P3, and the second substitution pump P2 according to the present embodiment are each a peristaltic pump that delivers liquid by squeezing a flexible tube forming a flow route.

The arterial blood circuit 1a and the venous blood circuit 1b are provided at distal ends thereof with respective connectors, through which an arterial puncture needle and a venous puncture needle (not illustrated) are connectable thereto. When the blood pump P1 is activated while a patient is punctured with the arterial puncture needle connected to the distal end of the arterial blood circuit 1a and the venous puncture needle connected to the distal end of the venous blood circuit 1b, blood of the patient can be made to extracorporeally circulate through the blood circuit 1.

Specifically, when the blood pump P1 is activated while the patient is punctured with the arterial puncture needle and the venous puncture needle, the patient's blood flows through the arterial blood circuit 1a and reaches the dialyzer 2, where the blood is purified. Then, the blood flows through the venous blood circuit 1b and returns into the patient's body. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The venous blood circuit 1b is provided with an air-trap chamber 3 at a halfway position thereof. The blood that extracorporeally circulates through the blood circuit 1 undergoes bubble removal in the air-trap chamber 3 and then returns into the patient. As an alternative to the embodiment in which a blood vessel of the patient is punctured with the arterial puncture needle and the venous puncture needle, the following may be taken: an embodiment in which a double-lumen catheter is inserted into the subclavian vein or the femoral vein of the patient, an embodiment in which a double-lumen catheter is inserted into a blood vessel in an arm of the patient, or the like.

The dialyzer 2 has a blood introduction port 2a allowing the blood to be introduced thereinto, a blood delivery port 2b allowing the blood to be delivered therefrom, a dialysate introduction port 2c allowing dialysate to be introduced thereinto, a dialysate delivery port 2d allowing the dialysate to be delivered therefrom, blood flow routes (not illustrated) extending between the blood introduction port 2a and the blood delivery port 2b and allowing the blood to flow therethrough, dialysate flow routes (not illustrated) extending between the dialysate introduction port 2c and the dialysate delivery port 2d and allowing the dialysate to flow therethrough, and blood purification membranes (not illustrated) separating the blood flow routes from the dialysate flow routes and through which the blood flowing in the blood flow routes is to be purified.

More specifically, the dialyzer 2 has the blood introduction port 2a, the blood delivery port 2b, the dialysate introduction port 2c, and the dialysate delivery port 2d all projecting from a housing thereof. The arterial blood circuit 1a is connected to the blood introduction port 2a. The venous blood circuit 1b is connected to the blood delivery port 2b. The dialysate introduction line L1 is connected to the dialysate introduction port 2c. The waste-liquid drain line L2 is connected to the dialysate delivery port 2d. For efficient dialysis treatment, the blood introduction port 2a as the inlet for the blood and the dialysate introduction port 2c as the inlet for the dialysate are positioned on the opposite sides in the vertical direction, so that the dialysate flows in a direction opposite to the direction in which the blood flows through the blood flow routes.

The dialyzer 2 houses a plurality of hollow fiber membranes formed of hollow fibers, serving as blood purification membranes for purifying the blood. Specifically, spaces inside the respective blood purification membranes formed of the hollow fibers serve as the blood flow routes, and spaces between the housing and the hollow fibers serve as the dialysate flow routes. The blood purification membranes as the hollow fiber membranes each have a number of microscopic holes (pores) extending therethrough from the outer surface to the inner surface. Impurities and the like contained in the blood flowing in the blood flow routes are allowed to permeate (to be filtered) through the hollow fiber membranes into the dialysate flowing in the dialysate flow routes.

The dialysate introduction line L1 is made of a flexible tube allowing the dialysate to flow therethrough and is connected to the dialysate introduction port 2c of the dialyzer 2. The waste-liquid drain line L2 is made of a flexible tube allowing the waste liquid to flow therethrough and is connected to the dialysate delivery port 2d of the dialyzer 2.

The first substitution line L3a is made of a flexible tube allowing substitution fluid stored in a substitution-fluid bag B (a substitution-fluid storage) to flow into the substitution-fluid temporary chamber K. The first substitution line L3a has one end connected to the bottom of the substitution-fluid bag B (the substitution-fluid storage), and the other end connected to the bottom of the substitution-fluid temporary chamber K. The substitution-fluid bag B stores a predetermined amount of substitution fluid to be supplied to the blood circuit 1 and is supported at a predetermined height by a supporting member (not illustrated) attached to the apparatus body. The substitution-fluid temporary chamber K receives the substitution fluid in the substitution-fluid bag B (the substitution-fluid storage) and is a case with a smaller capacity than the substitution-fluid bag B.

The first substitution line L3a is provided with the substitution-fluid transfer pump P4, which is a peristaltic pump that delivers liquid by squeezing a flexible tube forming a flow route for the substitution fluid. When the substitution-fluid transfer pump P4 is activated, a rotor rotates and rollers squeeze the flexible tube in the lengthwise direction. Thus, the substitution fluid stored in the substitution-fluid bag B can be delivered to and stored in the substitution-fluid temporary chamber K.

The second substitution line L3b is made of a flexible tube that allows the substitution fluid stored in the substitution-fluid temporary chamber K to flow into the blood circuit 1 through the pre-substitution line L3c or the post-substitution line L3d. The second substitution line L3b has one end connected to the bottom of the substitution-fluid temporary chamber K, and the other end connected to the pre-substitution line L3c and to the post-substitution line L3d. A combination of the first substitution line L3a and the second substitution line L3b corresponds to the substitution line according to the present invention.

The second substitution line L3b is provided with the first substitution pump P3, which is a peristaltic pump that delivers liquid by squeezing a flexible tube forming a flow route for the substitution fluid. When the first substitution pump P3 is activated, a rotor rotates and rollers squeeze the flexible tube in the lengthwise direction. Thus, the substitution fluid stored in the substitution-fluid temporary chamber K can be delivered for substitution to the arterial blood circuit 1a through the pre-substitution line L3c or to the venous blood circuit 1b through the post-substitution line L3d.

The second substitution line L3b according to the present embodiment is further provided with the heating device H for heating the substitution fluid. The heating device H is a heater capable of heating the substitution fluid to be introduced from the substitution-fluid temporary chamber K into the blood circuit 1. A heating bag 5 illustrated in FIG. 2 is attachable to the heating device H. The heating bag 5 has a flow route 5a obtained by, for example, fusing two flexible sheets to each other. The flow route 5a has connecting portions 5b and 5c at one end and the other end thereof, respectively, at which the flow route 5a is connectable to the second substitution line L3b.

The second substitution line L3b is further provided with an air-trap chamber 6 at a position between the heating device H and the arterial blood circuit 1a or the venous blood circuit 1b. The air-trap chamber 6 is capable of trapping bubbles in the substitution fluid. The bubbles in the substitution fluid heated by the heating device H are trapped in the air-trap chamber 6 and are therefore prevented from flowing into the blood circuit 1.

The pre-substitution line L3c is a flow route through which the substitution fluid is introduced into the arterial blood circuit 1a for pre-substitution. The pre-substitution line L3c has one end connected to the second substitution line L3b, and the other end connected to a position of the arterial blood circuit 1a that is between the blood pump P1 and the dialyzer 2. When the first substitution pump P3 is activated and the substitution fluid is delivered from the substitution-fluid temporary chamber K through the second substitution line L3b, the substitution fluid flows through the pre-substitution line L3c into the arterial blood circuit 1a.

The post-substitution line L3d is a flow route through which the substitution fluid is introduced into the venous blood circuit 1b for post-substitution. The post-substitution line L3d has one end connected to the second substitution line L3b, and the other end connected to the air-trap chamber 3 provided to the venous blood circuit 1b. When the first substitution pump P3 is activated and the substitution fluid is delivered from the substitution-fluid temporary chamber K through the second substitution line L3b, the substitution fluid flows through the post-substitution line L3d into the venous blood circuit 1b.

The pre-substitution line L3c according to the present embodiment is provided with the second substitution pump P2, which is a peristaltic pump that delivers liquid by squeezing a flexible tube forming a flow route for the substitution fluid. The post-substitution line L3d is provided with a check valve V1 that allows the substitution fluid to flow toward the blood circuit 1 but prevents the substitution fluid to flow toward the other side. The substitution pumps according to the present embodiment include the first substitution pump P3 provided to the substitution line (the second substitution line L3b) and the second substitution pump P2 provided to at least one of the pre-substitution line L3c and the post-substitution line L3d (in the present embodiment, the pre-substitution line L3c).

The second substitution line L3b corresponds to the substitution line according to the present invention. As illustrated in FIG. 1, the second substitution line L3b has one end connected to the substitution-fluid source (in the present embodiment, the substitution-fluid temporary chamber K) capable of supplying the substitution fluid, and the other end connected to the pre-substitution line L3c and to the post-substitution line L3d. Thus, the substitution fluid in the substitution-fluid source (the substitution-fluid temporary chamber K) is introduced into the arterial blood circuit 1a or the venous blood circuit 1b through the pre-substitution line L3c or the post-substitution line L3d. Furthermore, the substitution line (the second substitution line L3b) is provided with the first substitution pump P3, and the pre-substitution line L3c is provided with the second substitution pump P2.

Hence, when the second substitution pump P2 is activated at substantially the same flow rate as that of the first substitution pump P3, the substitution fluid in the substitution-fluid temporary chamber K can be introduced into the arterial blood circuit 1a for pre-substitution. On the other hand, when the first substitution pump P3 is activated with the second substitution pump P2 stopped, the substitution fluid in the substitution-fluid temporary chamber K can be introduced into the venous blood circuit 1b for post-substitution. Furthermore, when the second substitution pump P2 is activated at a flow rate lower than that of the first substitution pump P3, the substitution fluid can be introduced into both the arterial blood circuit 1a and the venous blood circuit 1b for pre- and post-substitution. The control unit 4 is capable of changing the ratio between the amount of pre-substitution and the amount of post-substitution by controlling the first substitution pump P3 and the second substitution pump P2 in such a manner as to change the flow-rate ratio between the first substitution pump P3 and the second substitution pump P2.

The post-substitution line L3d is provided with the check valve V1. Therefore, even if a negative pressure is generated in the flow route between the first substitution pump P3 and the second substitution pump P2, the blood in the blood circuit 1 can be prevented from being taken into the post-substitution line L3d. Note that a negative pressure is generated in the flow route between the first substitution pump P3 and the second substitution pump P2 when the flow rate of the second substitution pump P2 is higher than the flow rate of the first substitution pump P3. Other possible embodiments are as follows: an embodiment illustrated in FIG. 3 in which the pre-substitution line L3c is provided with the check valve V1 while the post-substitution line L3d is provided with the second substitution pump P2, and an embodiment illustrated in FIG. 4 in which the pre-substitution line L3c and the post-substitution line L3d are each provided with the second substitution pump P2.

The blood purification apparatus further includes a pressure sensor Pb that detects the fluid pressure in a portion of the flow route for the substitution fluid, the portion being enclosed by the first substitution pump P3, the second substitution pump P2, and the check valve V1 in the second substitution line L3b (the substitution line), the pre-substitution line L3c, and the post-substitution line L3d. The control unit 4 corrects the driving speed of the first substitution pump P3 or the second substitution pump P2 in accordance with the fluid pressure detected by the pressure sensor Pb.

For example, a control process executed by the control unit 4 when a negative pressure is generated in the portion of the flow route for the substitution fluid that is enclosed by the first substitution pump P3, the second substitution pump P2, and the check valve V1 in the second substitution line L3b (the substitution line), the pre-substitution line L3c, and the post-substitution line L3d will now be described with reference to the flow chart illustrated in FIG. 5. First, whether or not the pressure of the substitution fluid (the fluid pressure of the substitution fluid) detected by the pressure sensor Pb is lower than a specified value is checked (S1). If the pressure is determined to be lower than the specified value, the process proceeds to S2, where the driving speed of the second substitution pump P2, i.e. the pump on the downstream side, is reduced. If the pressure of the substitution fluid (the fluid pressure of the substitution fluid) detected by the pressure sensor Pb in S1 is determined to be higher than the specified value, S2 is skipped.

Meanwhile, the top of the substitution-fluid temporary chamber K is open to the atmosphere through an air filter F. Therefore, if any liquid stored in the substitution-fluid temporary chamber K is discharged, air is introduced into the temporary chamber K. If any liquid flows into the temporary chamber K, air is discharged from the temporary chamber K.

The control unit 4 controls the substitution pumps (the first substitution pump P3 and the second substitution pump P2) and is a microcomputer or the like provided on the apparatus body. In a measurement step, the control unit 4 according to the present embodiment introduces the dialysate into the dialyzer 2 and activates the first substitution pump P3 (the second substitution pump P2, according to need), thereby introducing the substitution fluid stored in the substitution-fluid temporary chamber K into the blood circuit 1. In this step, the substitution-fluid transfer pump P4 is kept stopped.

According to the present embodiment, the substitution pumps that deliver the substitution fluid in the substitution-fluid source (the substitution-fluid temporary chamber K) to the arterial blood circuit 1a or the venous blood circuit 1b include the first substitution pump P3 provided to the substitution line (the second substitution line L3b) and the second substitution pump P2 provided to at least one of the pre-substitution line L3c and the post-substitution line L3d. Therefore, pre-substitution and post-substitution can be performed in a good manner. Furthermore, even in a case where pre-substitution and post-substitution are performed simultaneously, the amount of substitution fluid consumed from the substitution-fluid source (the substitution-fluid temporary chamber K) can be grasped correctly.

The second substitution pump P2 according to the present embodiment is provided to only one of the pre-substitution line L3c and the post-substitution line L3d (in the present embodiment, only to the pre-substitution line L3c). Therefore, unlike the embodiment (see FIG. 4) in which the second substitution pump P2 is provided to each of the pre-substitution line L3c and the post-substitution line L3d, there is no need to synchronize two second substitution pumps P2. Consequently, the error in the amount of substitution fluid consumed through the pre-substitution line L3c and the amount of substitution fluid consumed through the post-substitution line L3d can be reduced.

The blood purification apparatus further includes the heating bag 5 to be heated by the heating device H and including a portion of the substitution line (the second substitution line L3b). Therefore, the substitution fluid flowing through the pre-substitution line L3c and the post-substitution line L3d can be heated by the heating device H. The heating bag 5 is attached to a position of the substitution line (the second substitution line L3b) that is between the first substitution pump P3 and a branching part of the pre-substitution line L3c and the post-substitution line L3d. That is, the heating bag 5 is provided at a predetermined position of the substitution line that is less affected by the negative pressure generated with the activation of the first substitution pump P3 and is before the branching part of the pre-substitution line L3c and the post-substitution line L3d. Therefore, the heating bag 5 can be provided regardless of whether the material thereof is soft or hard. Furthermore, the number of heating bags 5 can be reduced, leading to a reduction in the heating-bag cost.

The substitution line (the second substitution line L3b) is provided with the air-trap chamber 6 at a position between the heating device H and the arterial blood circuit 1a or the venous blood circuit 1b, the air-trap chamber 6 being capable of trapping bubbles in the substitution fluid. Therefore, bubbles generated in the substitution fluid when the substitution fluid is heated by the heating device H can be assuredly trapped and removed by the air-trap chamber 6.

Alternatively, as illustrated in FIG. 6, the air-trap chamber 6 may be provided to the pre-substitution line L3c, so that bubbles in the substitution fluid flowing through the pre-substitution line L3c can be trapped in the air-trap chamber 6, and bubbles in the substitution fluid flowing through the post-substitution line L3d can be trapped in the air-trap chamber 3 provided to the venous blood circuit 1b.

The first substitution pump P3 and the second substitution pump P2 are each a peristaltic pump that delivers liquid by squeezing a flexible tube forming a flow route for the substitution fluid. Furthermore, the first substitution pump P3 and the second substitution pump P2 are provided to the substitution line (the second substitution line L3b) and the pre-substitution line L3c (or the post-substitution line L3d), respectively. Therefore, the flow route for the substitution fluid can be closed by stopping the peristaltic pumps, without providing any separate clamping units or the like.

One of the pre-substitution line L3c and the post-substitution line L3d is provided with the second substitution pump P2, and the other is provided with the check valve V1. Therefore, even if a negative pressure is generated between the first substitution pump P3 and the second substitution pump P2, the check valve V1 can prevent the blood in the blood circuit 1 from being taken into the pre-substitution line L3c or the post-substitution line L3d.

The blood purification apparatus further includes the pressure sensor Pb that detects the fluid pressure in the portion of the flow route for the substitution fluid that is enclosed by the first substitution pump P3, the second substitution pump P2, and the check valve V1 in the substitution line (the second substitution line L3b), the pre-substitution line L3c, and the post-substitution line L3d (the fluid pressure in a portion between the first substitution pump P3 and the second substitution pump P2 in the substitution line, the pre-substitution line L3c, and the post-substitution line L3d). The control unit 4 corrects the driving speed of the first substitution pump P3 or the second substitution pump P2 in accordance with the fluid pressure detected by the pressure sensor Pb. Therefore, even if a negative pressure or a positive pressure is generated in the portion of the flow route for the substitution fluid that is enclosed by the first substitution pump P3, the second substitution pump P2, and the check valve V1 in the substitution line (the second substitution line L3b), the pre-substitution line L3c, and the post-substitution line L3d, the negative pressure or the positive pressure can be removed by correcting the driving speed of the first substitution pump P3 or the second substitution pump P2.

While some embodiments have been described above, the present invention is not limited thereto. For example, as illustrated in FIG. 7, the substitution-fluid bag B as the substitution-fluid source may be directly connected to the substitution line L3b, without providing the substitution-fluid temporary chamber K. In such a case, the substitution line L3b is provided with the first substitution pump P3, and at least one of the pre-substitution line L3c and the post-substitution line L3d (in the drawing, only the pre-substitution line L3c) is provided with the second substitution pump P2. The substitution-fluid bag B, which is a flexible case, may be replaced with a substitution-fluid storage such as a hard case or a liquid tank. As in the present embodiment, it is desirable that the heating bag 5 be provided only at a position of the substitution line (the second substitution line L3b) that is between the first substitution pump P3 and the branching part of the pre-substitution line L3c and the post-substitution line L3d. Alternatively, the heating bag 5 may be provided at another position. For example, the heating bag 5 may be provided to each of the pre-substitution line L3c and the post-substitution line L3d. While the present embodiment concerns a case where a single heating bag 5 is provided at a position of the substitution line (the second substitution line L3b) that is between the first substitution pump P3 and the branching part of the pre-substitution line L3c and the post-substitution line L3d, a plurality of heating bags 5, for example, may be provided (the heating bag 5 may be divided into a plurality of separate bags).

The blood purification apparatus may have other additional functions or the like, as long as the apparatus includes substitution pumps including a first substitution pump provided to a substitution line, and a second substitution pump provided to at least one of a pre-substitution line and a post-substitution line.

REFERENCE SIGN LIST 1 blood circuit
1a arterial blood circuit
1b venous blood circuit
2 dialyzer (blood purifier)
3 air-trap chamber
4 control unit
5 heating bag
6 air-trap chamber
K substitution-fluid temporary chamber
B substitution-fluid bag (substitution-fluid storage)
L1 dialysate introduction line
L2 waste-liquid drain line
L3a first substitution line
L3b second substitution line
L3c pre-substitution line
L3d post-substitution line
P1 blood pump
P2 second substitution pump
P3 first substitution pump
P4 substitution-fluid transfer pump
H heating device

The invention claimed is:

1. A blood purification apparatus comprising:
a blood circuit including an arterial blood circuit and a venous blood circuit and that allows a patient's blood to extracorporeally circulate, with a blood purifier that is interposed between the arterial blood circuit and the venous blood circuit and purifies the patient's blood;
a pre-substitution line through which substitution fluid is introduced into the arterial blood circuit for pre-substitution;
a post-substitution line through which the substitution fluid is introduced into the venous blood circuit for post-substitution;
a substitution line having one end connected to a substitution-fluid source capable of supplying the substitution fluid, and an other end connected to the pre-substitution line and to the post-substitution line;
substitution pumps that deliver the substitution fluid in the substitution-fluid source from the substitution line through at least one of the pre-substitution line and the post-substitution line to at least one of the arterial blood circuit and the venous blood circuit;
a control unit that controls the substitution pumps,
a heating bag to be heated by a heating device and including a portion of the substitution line, the heating bag being attached to a position of the substitution line that is between a first substitution pump and a branching part of the pre-substitution line and the post-substitution line;
an air trap chamber, wherein the substitution line is provided with the air-trap chamber at a position between the heating device and the arterial blood circuit or the venous blood circuit, the air-trap chamber being capable of trapping bubbles in the substitution fluid;
wherein the substitution pumps are each a peristaltic pump that deliver liquid by squeezing a flexible tube forming a flow route for the substitution fluid, and include a first substitution pump provided to the substitution line, and a second substitution pump provided to one of the pre-substitution line and the post-substitution line,
the blood purification apparatus further comprises:
a check valve provided to one of the pre-substitution line and the post-substitution line, wherein the check valve is located within the post-substitution line between the air-trap chamber and a dialyzer; and
a pressure sensor that detects a fluid pressure in a portion between the first substitution pump and the second substitution pump in the substitution line, the pre-substitution line, and the post-substitution line;
wherein the control unit corrects a driving speed of the first substitution pump or the second substitution pump in accordance with the fluid pressure detected by the pressure sensor to remove a negative pressure or a positive pressure generated in the portion of the flow route for the substitution fluid between the first substitution pump and the second substitution pump in the substitution line, the pre-substitution line, and the post-substitution line.

2. The blood purification apparatus according to claim 1, wherein one of the pre-substitution line and the post-substitution line is provided with the second substitution pump, and an other is provided with the check valve.

3. The blood purification apparatus according to claim 1, wherein when a flow rate of the second substitution pump is set higher than the flow rate of the first substitution pump, pre-substitution and post-substitution are performed simultaneously.

4. The blood purification apparatus according to claim 1, wherein the check valve is located within the pre-substitution line between the dialyzer and the air-trap chamber.

5. The blood purification apparatus according to claim 1, wherein the check valve is located within the post-substitution line between the air-trap chamber and the heating bag.

* * * * *